United States Patent
Distler et al.

(10) Patent No.: US 7,867,701 B2
(45) Date of Patent: Jan. 11, 2011

(54) METHOD FOR THE SIMULTANEOUS AMPLIFICATION OF MULTIPLE SEQUENCES IN A PCR REACTION AND MARKING THEREOF

(75) Inventors: Jürgen Distler, Berlin (DE); Kurt Berlin, Stahnsdorf (DE); Alexander Olek, Berlin (DE)

(73) Assignee: Epigenomics AG, Berlin (DE)

( * ) Notice: Subject to any disclaimer, the term of this patent is extended or adjusted under 35 U.S.C. 154(b) by 655 days.

(21) Appl. No.: 10/451,646

(22) PCT Filed: Dec. 22, 2001

(86) PCT No.: PCT/DE01/04951

§ 371 (c)(1), (2), (4) Date: Jun. 23, 2003

(87) PCT Pub. No.: WO02/052040

PCT Pub. Date: Jul. 4, 2002

(65) Prior Publication Data

US 2004/0067508 A1    Apr. 8, 2004

(30) Foreign Application Priority Data

Dec. 22, 2000   (DE)   ................. 100 65 814

(51) Int. Cl.
C12Q 1/68 (2006.01)
C12P 19/34 (2006.01)
C07H 21/04 (2006.01)

(52) U.S. Cl. .............. 435/6; 435/91.2; 536/24.33
(58) Field of Classification Search ............ 435/6, 435/91.2; 536/24.33
See application file for complete search history.

(56) References Cited

U.S. PATENT DOCUMENTS

| | | | | |
|---|---|---|---|---|
| 5,512,441 | A | * | 4/1996 | Ronai ................... 435/6 |
| 5,744,306 | A | | 4/1998 | Murtagh, Jr. et al. |
| 5,882,856 | A | * | 3/1999 | Shuber .................. 435/6 |
| 6,214,556 | B1 | * | 4/2001 | Olek et al. ............. 435/6 |

FOREIGN PATENT DOCUMENTS

WO    WO 01/07647 A2    2/2001

OTHER PUBLICATIONS

Schuelke M. An economic method for the fluorescent labeling of PCR fragments. Nature Biotechnology, vol. 18, pp. 233-234, Feb. 2000.*
Olek et al., "A modified and improved method for bisulphite based cytosine methylation analysis," Nucleic Acids Research, 24(24):5064-6 (1996).
Zeschnigk et al., Eur. J. Hum. Genet., 5:94-8 (1997).
Schuelke, "An economic method for the fluorescent labeling of PCR fragments," Nature Biotechnology, 18:233-4 (Feb. 2000).

* cited by examiner

*Primary Examiner*—Suryaprabha Chunduru
(74) *Attorney, Agent, or Firm*—Kriegsman & Kriegsman

(57) ABSTRACT

A method is described for the amplification of nucleic acids, in which the segments to be amplified are first hybridized with at least two primer oligonucleotides that have two domains, wherein the sequence-specific domain found at the 3-end hybridizes to the segment to be amplified, while the generic domain found at the 5-end does not hybridize. Then an amplification reaction is conducted by means of a polymerase and subsequently a labeled primer oligonucleotide, which binds to the generic domain of the first primer, is hybridized to the amplificate which is formed. In the last step, the sequence of the amplificate is investigated.

15 Claims, 4 Drawing Sheets

US 7,867,701 B2

METHOD FOR THE SIMULTANEOUS AMPLIFICATION OF MULTIPLE SEQUENCES IN A PCR REACTION AND MARKING THEREOF

FIELD OF THE INVENTION

The invention refers to the particularly rational production of complex, labeled amplificates in a PCR reaction. The sequences of these amplificates can subsequently be investigated by means of the most varied methods. The method is particularly suitable for the analysis of cytosine methylation patterns in DNA samples.

PRIOR ART

The polymerase chain reaction (PCR) is a method by means of which, in principle, any DNA can be selectively amplified. This method comprises the use of a set of at most two oligonucleotides with predefined sequence, so-called primers, which hybridize to DNA strands that are complementary to them and define the boundaries of the sequence to be amplified.

The oligonucleotides initiate the DNA synthesis, which is catalyzed by a heat-stable DNA polymerase. Each round of synthesis is typically separated by a melting and re-annealing step. This technique permits amplification of a given DNA sequence by several hundred times in less than one hour.

PCR has gained a wide acceptance due to the simplicity and reproducibility of these reactions. For example, PCR is used for the diagnosis of hereditary malfunctions and when such diseases are suspected.

Often, however, an amplification of a given sample is also conducted simply to propagate the material for a subsequent investigation. The sample to be investigated is first amplified in this case, either starting from genomic DNA, or, e.g., isolated mRNA. For the most part, it is necessary to label at least one of the primers, e.g., with a fluorescent substance, in order to be able to identify the fragment in subsequent experiments.

The method of using primers that have two domains represents a particularly simple and cost-effective variant for introducing a label onto the amplificates. One of these domains hybridizes specifically to the region to be amplified, while the other only has the function of hybridizing with a labeled oligonucleotide. This [labeled] oligonucleotide can always be the same one for the most varied amplifications, if the same primer domain responsible for the label is always used. This is a cost-effective solution, particularly for expensive labels. For example, three different oligonucleotides are utilized for this reaction:

a sequence-specific forward primer with an M13(−21) tail, a sequence-specific reverse primer, and a universal fluorescently labeled M13 (−21) oligonucleotide (Schuelke et al., An economic method for the fluorescent labeling of PCR fragments 2: 18, 2000), which binds to the M13(−21) tail of the forward primer.

This amplified DNA is utilized for the identification of mutations and polymorphisms. The following analytical methods are used for this: e.g., the primer extension reaction, sequencing according to Sanger, or, e.g., restriction digestion and subsequent investigation on agarose gels, for example.

For the investigation of DNA via the investigation of the base sequence, frequently the ratio of the DNA bases cytosine to 5-methylcytosine is drawn on, or individual cytosine positions are investigated for methylation.

5-Methylcytosine is the most frequent covalently modified base in the DNA of eukaryotic cells. For example, it plays a role in the regulation of transcription, in genetic imprinting and in tumorigenesis. The identification of 5-methylcytosine as a component of genetic information is thus of considerable interest. 5-Methylcytosine positions, however, cannot be identified by sequencing, since 5-methylcytosine has the same base-pairing behavior as cytosine. In addition, in the case of a PCR amplification, the epigenetic information which is borne by the 5-methylcytosines is completely lost.

A relatively new method that in the meantime has become the most widely used method for investigating DNA for 5-methylcytosine is based on the specific reaction of bisulfite with cytosine, which, after subsequent alkaline hydrolysis, is then converted to uracil, which corresponds in its base-pairing behavior to thymidine. In contrast, 5-methylcytosine is not modified under these conditions. Thus, the original DNA is converted so that methylcytosine, which originally cannot be distinguished from cytosine by its hybridization behavior, can now be detected by "standard" molecular biology techniques as the only remaining cytosine, for example, by amplification and hybridization or sequencing. All of these techniques are based on base pairing, which is now fully utilized. The prior art, which concerns sensitivity, is defined by a method that incorporates the DNA to be investigated in an agarose matrix, so that the diffusion and renaturation of the DNA is prevented (bisulfite reacts only on single-stranded DNA) and all precipitation and purification steps are replaced by rapid dialysis (Olek A, Oswald J, Walter J. A modified and improved method for bisulphite based cytosine methylation analysis. Nucleic Acids Res. Dec. 15, 1996; 24(24): 5064-6). Individual cells can be investigated by this method, which illustrates the potential of the method. Of course, up until now, only individual regions of up to approximately 3000 base pairs long have been investigated; a global investigation of cells for thousands of possible methylation analyses is not possible. Of course, this method also cannot reliably analyze very small fragments of small quantities of sample. These are lost despite the protection from diffusion through the matrix.

An overview of other known possibilities for detecting 5-methylcytosines can be derived from the following review article: Rein T, DePamphilis M L, Zorbas H. Identifying 5-methylcytosine and related modifications in DNA genomes. Nucleic Acids Res. May 15, 1998; 26(10): 2255-64.

The bisulfite technique has been previously applied only in research, with a few exceptions (e.g., Zeschnigk M, Lich C, Buiting K, Doerfler W, Horsthemke B. A single-tube PCR test for the diagnosis of Angelman and Prader-Willi syndrome based an allelic methylation differences at the SNRPN locus. Eur J Hum Genet 1997 March-April; 5(2):94-8). However, short, specific segments of a known gene have always been amplified after a bisulfite treatment and either completely sequenced (Olek A, Walter J. The pre-implantation ontogeny of the H19 methylation imprint. Nat Genet. 1997 November; 17(3): 275-6) or individual cytosine positions have been detected by a "primer extension reaction" (Gonzalgo M L, Jones P A. Rapid quantitation of methylation differences at specific sites using methylation-sensitive single nucleotide primer extension (Ms-SNuPE). Nucleic Acids Res. Jun. 15, 1997; 25(12): 2529-31, WO-Patent 95-00669) or an enzyme step (Xiong Z, Laird P W. COBRA: a sensitive and quantitative DNA methylation assay. Nucleic Acids Res. Jun. 15, 1997; 25(12): 2532-4). Detection by hybridization has also been described (Olek et al., WO-A 99-28498).

Other publications which are concerned with the application of the bisulfite technique for the detection of methylation in the case of individual genes are: Grigg G, Clark S. Sequencing 5-methylcytosine residues in genomic DNA. Bioessays. 1994 June; 16(6): 431-6, 431; Zeschnigk M, Schmitz B, Dittrich B, Buiting K, Horsthemke B, Doerfier W. Imprinted segments in the human genome: different DNA methylation patterns in the Prader-Willi/Angelman syndrome region as determined by the genomic sequencing method. Hum Mol Genet. 1997 March; 6(3): 387-95; Feil R, Charlton J, Bird A P, Walter J, Reik W. Methylation analysis on individual chromosomes: improved protocol for bisulphite genomic sequencing. Nucleic Acids Res. Feb. 25, 1994; 22(4): 695-6; Martin V, Ribieras S, Song-Wang X, Rio M C, Dante R. Genomic sequencing indicates a correlation between DNA hypomethylation in the 5' region of the pS2 gene and in its expression in human breast cancer cell lines. Gene. May 19, 1995; 157(1-2): 261-4; WO 97-46705, WO 95-15373 and WO 45560.

To analyze PCR products, they must be provided, e.g., with a fluorescent label or a radioactive label. These labels can be introduced either on the primers or on the nucleotides. Particularly suitable for fluorescent labels is the simple introduction of Cy3 and Cy5 dyes at the 5'-end of the respective primer. The following are also considered as fluorescent dyes: 6-carboxyfluorescein (FAM), hexachloro-6-carboxyfluorescein (HEX), 6-carboxy-x-rhodamine (ROX) or tetrachloro-6-carboxyfluorescein (TET). These dyes are, however, comparatively more expensive.

For the analysis of genes, in which the mutated allele or the polymorphism is well characterized, the amplification of individual defined regions of the DNA is sometimes sufficient. However, if undefined genes are analyzed, for the most part a plurality of PCR reactions are necessary in order to identify critical deletions or changes of bases. Even more complicated is the establishment of a multiplex PCR, in which a forward primer and a plurality of reverse primers are used, in order to amplify defined gene segments.

Whereas the annealing temperature and the primer concentration can be calculated to a certain extent, the conditions for each individual multiplex reaction must generally be determined experimentally. Since the probability of a nonspecific initial reaction increases with each additional primer, for the most part, the conditions must be modified for further primer additions. Also, the artifacts which arise due to the competition for resources are multiplied, e.g., by the [number of] primers in the multiplex PCR. This results in the circumstance that yields of unequally amplified fragments increase with each cycle.

Due to the difficulties discussed above, the development of a new diagnostic test can be labor- and cost-intensive.

Weighardt et al. (PCR Methods and App. 3:77, 1993) describe the use of 5'-extended oligonucleotides for PCR. This amplification method contains as its characteristic feature a separate annealing and primer extension reaction for each individual primer, which cannot be carried out in a multiplex context.

As pointed out, it is currently state of the art to treat the sample DNA with bisulfite and then to conduct simple amplifications in order to identify cytosine methylation. A method is lacking, however, which permits conducting, by means of primers with two domains, a particularly specific two-step amplification, which most specifically prepares a plurality of fragments simultaneously and also which solves the problem whereby normally a plurality of labeled and correspondingly expensive primers would have to be utilized for such a complex amplification.

PRESENTATION OF THE PROBLEM

A method will be provided, which overcomes the disadvantages of the prior art. First, a very specific 2-step PCR with high multiplexing capacity will be provided, which also solves the problem of cost-intensive labels. The method will be particularly suitable for the detection of cytosine methylation in DNA samples.

DESCRIPTION

A method is described for the amplification of nucleic acids.

The nucleic acids are most preferably obtained from a genomic DNA sample, whereby the sources for DNA include, e.g., cell lines, blood, sputum, stool, urine, cerebrospinal fluid, tissue embedded in paraffin, for example, tissue from eyes, intestine, kidney, brain, heart, prostate, lung, breast or liver, histological slides and all possible combinations thereof.

The nucleic acid sample is most preferably embedded in agarose and reacted with a bisulfite solution (=disulfite, hydrogen sulfite), whereby 5-methylcytosine remains unchanged and cytosine is converted to uracil or another base similar to uracil in its base-pairing behavior. In this chemical treatment, a reagent that denatures the DNA duplex and/or a radical trap are [also] present.

Since in the human genome, only approximately 3% of the cytosine bases are present in the methylated state, bisulfite-treated DNA for the most part contains the bases A, G, T and U; that is, only 3 bases (A, G and T) with respect to their base-pairing behavior, since U and T show the same pairing behavior.

Then the segments to amplified are hybridized with at least two primer oligonucleotides, which have two domains: the sequence-specific domain found on the 3'-end hybridizes to the segment to be amplified, while the generic domain found on the 5'-end does not hybridize. In the next step, a first amplification reaction is conducted by means of a polymerase. In a further step, a labeled primer oligonucleotide, which hybridizes to the generic domain of the first primer, hybridizes to the amplificate. A second amplification reaction with a polymerase [chain] reaction is preferably conducted.

A heat-stable DNA polymerase is most preferably used for the amplification.

If bisulfite-treated DNA is amplified, this DNA fragments are produced, which are characterized in that the (+)-strand has the base composition A, T and G, and its inversely complementary (−)-strand has the base composition A, T and C. It therefore results that the C and G nucleobases are never or very seldom present simultaneously in the (+)- or (−)-strand. Due to this property of bisulfite-treated DNA and its amplification products, it is possible to prepare primers, which do not produce nonspecific PCR products with bisulfite template DNA and thus can be used as generally applicable labeling oligonucleotides or detection probes for PCR amplificates of bisulfite-treated DNA.

The prerequisite for this is that gene-specific primers of types 1 and 2 are designed for the amplification of bisulfite-treated DNA, which [primers] possess a generic domain in addition to a gene-specific domain. These generic primer domains make possible the labeling of the DNA fragments with the generally applicable oligonucleotide labels (type M1 and type M2) or their detection with these general oligonucleotide labels (type M1 and type M2) due to hybridization behavior. For the amplification of specific genes or several genes in a multiplex PCR, at least 2 primers are necessary, one primer of type 1 and the second of type 2 (see below). The corresponding DNA fragments are amplified with these primers.

Structure and Properties of the Primers

```
Primer type 1:
generic domain                                                              gene-specific domain
5'----------------------------------------------------------------------------------3'
contains A, T, C, G                                                         contains A, T, G Primer type 2:
generic domain                                                              gene-specific domain
5'----------------------------------------------------------------------------------3'
contains A, T, C, G                                                         contains A, T, C
```

Primer Type M1:
   Sequence identical to generic domain of the type 1 primer

```
Mod-5'-------------------------------------------------------------------------------3'
contains A, T, C, G, Mod. Modification or label
```

Primer Type M2:
   Sequence identical to complementary sequence of the generic domain of the type 2 primer

```
Mod-5'-------------------------------------------------------------------------------3'
contains A, T, C, G, Mod. Modification or label
```

The generic domain of the type 1 and type 2 primers preferably contains a sequence which is comprised of A, C, G and T.

As the name suggests, the gene-specific domains are specific for one or more gene fragment(s). In the case of sequence-specific primers of type 1, the sequence is comprised of A, T, and G bases, and in the case of sequence-specific primers of type 2, it is comprised of A, T, and C bases.

In a second PCR reaction with a generic primer pair of the M1 and M2 type, these genes or an arbitrary number of genes that are formed from PCR reactions with primer pairs (type 1 and type 2) are simultaneously reamplified, whereby all type 1 primers and the type 2 primers possess identical generic domains (Examples 2 and 3). The generic domains of the type 1 and 2 primers are designed in such a way that the corresponding generic primer labels (type M1 and type M2) produce almost no nonspecific PCR product in a PCR reaction with the bisulfite template DNA that is used. The PCR reactions can be conducted sequentially or, due to suitable selection of the gene-specific and generic primers, as well as conducting the PCRs, they can be conducted simultaneously in a so-called one-pot reaction.

Due to their hybridization behavior, generic primers of the M1 and M2 type can also be used for the detection of PCR amplificates, which were produced with type 1 and type 2 primers and then, for example, were immobilized on DNA arrays, nitrocellulose membranes, PVDF membranes or other solid surfaces.

The amplified segments which have been formed from PCR fragments with primers having two domains can be immobilized on solid phases. This is done by chemical reactions (e.g., by introducing a 5'-amino function) or by hybridization to other oligonucleotides immobilized on the solid phase. The amplificates can thus be dectected by the labeled generic primers of the M1/M2 type. The labels that are introduced on the amplificates at each position of the solid phase at which an oligonucleotide is found can preferably be identified.

If PNA oligomers of the M1 and M22 [sic] type are used as the generic primers, however, instead of DNA oligomers, PCR amplificates, which are produced with type 1 and type 2 primers, can also be identified and quantified by MALDI-TOF.

The labels of oligonucleotide primers preferably involve fluorescent dyes with different emission spectra (e.g., Cy3, Cy5, FAM, HEX, TET or ROX) or fluorescent dye combinations in the case of primers labeled by energy-transfer fluorescent dye. The labels can preferably be radionuclides or preferably removable mass labels, which are detected in a mass spectrometer. Molecules, which only produce a signal in a further chemical reaction, may also be preferably used for labeling. The molecules used for the labels are preferably bound to defined positions on a solid phase, in order to immobilize the PCR products, which result from a PCR reaction and domain primers, via a solid-phase PCR.

The PCR fragments are preferably arranged on the solid phase in the form of a rectangular or hexagonal grid.

Lastly, the sequence of the amplificate is investigated.

The described DNA modification is produced by the use of identical primer pairs with an identical fragment-specific modification, i.e., all labels are identical and result in the same specific reaction. By means of these simplifications, considerable costs can be saved, since dye or mass labels, in particular, involve high costs.

The method is preferably used for the diagnosis and/or prognosis of adverse events for patients or individuals, whereby these adverse events belong to at least one of the following categories: undesired drug interactions; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as the consequence of an abnormality in the development process; malfunction, damage or disorder of the skin, the muscles, the connective tissue or the bones, endocrine and metabolic malfunction damage or disease; headaches or sexual malfunction.

The method is most preferably used for distinguishing cell types or tissues or for investigating cell differentiation.

The following examples explain the invention:

EXAMPLE 1

Design and Construction of Gene-Specific and Modular Primers

The sequences present after a bisulfite treatment were determined for each of the genes OAT (ACCESSION ep30056) and MDR1 (ACCESSION X58723). Based on these chemically pretreated DNA sequences (see Appendix), the following gene-specific primer domains were prepared and investigated with commercially obtainable analytical software, in order to exclude self-complementary or inter-complementary sequence regions in the primer sequences (see Tables 1 and 2). These sequences were converted to non-modular PCR primers OAT-fp, OAT-rp, MDR-fp and MDR-rp, and tested for their function in PCR reactions. With their use in PCR reactions (see Example 2) with bisulfite DNA, produced according to published methods (Olek et al., Nucl. Acids. Res. 1996, 24, 5064-5066), the primer combinations for OAT and MDR1 supplied the expected products of 479 nt and 633 nt (see Table 1). As the sequence for the generic primer domains, gen1-f, corresponding to the sequence of the M13 universal sequencing primer and gen2-f (Table 2), as well as gen-r corresponding to the reverse M13 sequencing primer were selected. The corresponding non-modular primers based on these sequences showed no recognizable PCR products in the PCR reaction on bisulfite DNA under various reaction conditions, for the primer pair combinations gen1-fp, gen-rp, as well as gen2-fp, gen-rp.

The modular primers for the amplification of OAT and MDR1 gene regions are produced the fusion of the generic sequences with the corresponding gene-specific domains, in order to obtain the modular primers OAT-F1mp, OAT-f2mp, OAT-rmp, MDR-f1mp, MDR-f2mp and MDR-rmp (Table 3).

TABLE 1

Gene-specific and generic primer domains

| Gene | Forward primer | Reverse primer | PCR fragment |
|---|---|---|---|
| OAT | OAT-f | OAT-r | 479 nt |
| MDR1 | MDR-f | MDR-r | 633 nt |
| Generic | gen1-f | gen-r | |
| | gen2-f | | |

TABLE 2

Non-modular primer sequences

| OAT-fp | TTTGGAGGTGGATTTAGAGGTATAAATTAA |
| OAT-rp | AAACRTCACTACAACTTAAAAACTAA |
| MDR-fp | TAAGTATGTTGAAGAAAGATTATTGTAG |
| MDR-rp | TAAAACTATCCCATAATAACTCCCAAC |
| gen1-fp | GTAAAACGACGGCCAGT |
| gen2-rp | GTAAAACCAGGGCCAGT |
| gen-rp | CAGGAAACAGCTATGAC |
| gen1-fp5 | Cy5-GTAAAACGACGGCCAGT |
| gen2-rp5 | Cy5-GTAAAACCAGGGCCAGT |
| gen-rp5 | Cy5-CAGGAAACAGCTATGAC |

TABLE 3

Modular primers

| Name | Sequence Generic domain - Gene-specific domain |
|---|---|
| OAT-f1mp | GTAAAACGACGGCCAGT-TTGGAGGTGGATTTAGAGGTATAATTAA |
| OAT-f2mp | GTAAAACCAGGGCCAGT-TTGGAGGTGGATTTAGAGGTATAATTAA |
| OAT-rmp | CAGGAACAGCTATGAC-AAACRTCACTACAACTTAAAAACTAA |
| NDR-f1mp | GTAAAACGACGGCCAGT-TAAGTATGTTGAAGAAAGATTATTGTAG |
| MDR-f2mp | GTAAAACCAGGGCCAGT-TAAGTATGTTGAAGAAAGATTATTGTAG |
| MDR-rmp | CAGGAAACAGCTATGAC-TAAAACTATCCCATAATAACTCCCAAC |

EXAMPLE 2

Gene-Specific Amplification of OAT and MDR1 with Modular Primers

The amplification of OAT and MDR1 gene regions was conducted with Qiagen Hotstart Polymerase according to the manufacturer's instructions (Qiagen, Hilden) in a reaction volume of 20 µl.

| Reaction batch (general) | |
|---|---|
| Bisulfite DNA (10 ng) | 1 µl |
| Reaction buffer 10x (Qiagen, Hilden) | 2 µl |
| dNTP mix (10 mM each) | 2 µl |
| Primer 1 6.25 pmol | 2 µl |
| Primer 2 6.25 pmol | 2 µl |
| Polymerase (Qiagen, Hilden) (0.5 U) | 0.5 µl |
| Water | 11.5 µl |

The PCR reaction was conducted in the Master Cycler Gradient (Eppendorf, Hamburg) with the following program.

Program:

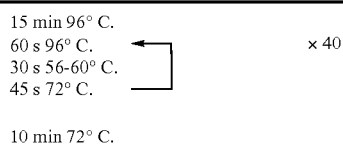

10 min 72° C.

The primer combinations and annealing temperatures used for the amplification of OAT and MDR1 are compiled in Table 4. The PCR amplificates produced were analyzed by agarose gel electrophoresis (1.5% agarose in 0.5×TBE buffer, Manniatis et al.). For this purpose, 4 μl of the PCR batch were subjected to gel electrophoresis and the result is shown in FIG. 1.

TABLE 4

PCR Primer Combinations

| Gene | Primer 1 | Primer 2 | Annealing temp. | Lane in FIG. 1 |
|---|---|---|---|---|
| OAT | OAT-f1mp | OAT-rmp | 55, 6° C. | A |
| OAT | OAT-f2mp | OAT-rmp | 55, 6° C. | B |
| MDR1 | MDR-f1mp | MDR-rmp | 59° C. | C |
| MDR1 | MDR-f2mp | MDR-rmp | 59° C. | D |

[type, paste]

EXAMPLE 3

Reamplification of OAT and MDR1 with Generic Primers

The reamplification (=label amplification) of OAT and MDR1 gene regions was conducted with Qiagen Hotstart Polymerase according to the manufacturer's instructions (Qiagen, Hilden) in a reaction volume of 20 μl. The PCR products from the gene-specific PCR (see Example 2, FIG. 1) were diluted 1:1000 and amplified separately or jointly in a PCR reaction. The following were used as primers: the primer pairs gen1-fp5 and gen-rp5, as well as gen2-fp5 and gen-rp5 modified at the 3'-end with the fluorescent dye, Cy5. The results of this label amplification are shown in FIG. 2.

| Reaction batch (general): | |
|---|---|
| Template DNA | 1 μl |
| Reaction buffer 10x (Qiagen, Hilden) | 2 μl |
| dNTP mix (10 mM each) | 2 μl |
| Primer pair (6.25 pmol per primer) | 4 μl |
| Polymerase (Qiagen, Hilden) (0.5 U) | 0.5 μl |
| Water | 11.5 μl |

The PCR reaction was conducted in the Master Cycler Gradient (Eppendorf, Hamburg) with the following program.

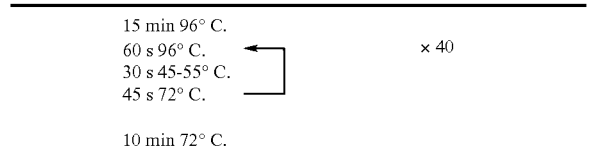

The PCR amplificates produced were analyzed by agarose gel electrophoresis (1.5% agarose in 0.5×TBE buffer, Manniatis et al.). For this purpose, 4 ul of the PCR batch were subjected to gel electrophoresis and the result is shown in FIG. 2. Under the indicated conditions, both OAT und MDR1 could be amplified successfully with the two generic primer pairs and thus are simultaneously and identically modified in a PCR reaction.

EXAMPLE 4

Reamplification with a Domain Primer

The bisulfite sequence was replaced by ESR1. The following gene-specific primer domains were prepared on the basis of this DNA sequence (see the ESR1-PCR product below), and investigated with commercially obtainable analytical software, in order to exclude self-complementary or inter-complementary sequence regions in the primer sequences (see Table 5). These sequences were converted into modular PCR primers ER1-B-U-M13a, ER1-B-L-M13b, ER1-B-U-M13b, ER1-B-L-M13a as well as the non-modular PCR primers ER1-B-U, ER1-B-L and tested for their function in PCR reactions. The modular primers for the amplification of ESR1 gene regions are produced by the fusion of the generic sequences M13a and M13b with the gene-specific domains ER1-B-U and ER1-B-L (Table 5). The primer combinations ER1-B-L-M13b/ER1-B-L-M13a, ER1-B-U-M13a/ER1B-L-M13a, ER1-B-L-M13b/ER1-B-U-M13b and ER1-B-U/ER1-B-L, when used in the PCR reactions (see FIG. 3, lanes 1-4) with bisulfite-treated DNA, supplied the expected products of 699 nt (modular primer) and 665 nt (non-modular primer). In contrast, no PCR products were obtained, if chemically untreated DNA was utilized in the PCR reaction (see FIG. 3, lanes 5-8). The PCR reaction batch had the following composition:

| | |
|---|---|
| DNA (10 ng) | 1 μl |
| Reaction buffer 10x (Qiagen, Hilden) | 2.5 μl |
| dNTP mix (25 mM each) | 0.2 μl |
| Primer 1 12.5 pmol | 1 μl |
| Primer 2 12.5 pmol | 1 μl |
| Polymerase (Qiagen, Hilden) (0.5 U) | 0.2 μl |
| Water | 19.1 μl | and was conducted with the following cycling program: 15 min 96° C.; 60 s 96° C. (×40); 45 s 55° C. (×40); 75 s 72° C. (×40); 10 min 72° C.

Table 5: Gene-Specific, Modular and Generic Primers for the Amplification of ESR1

| | Name | Sequence |
|---|---|---|
| A | ER1-B-U-M13a | GTAAAACGACGGCCAGTAGGAGGGGGAATTAAATAGA |
| B | ER1-B-L-M13b | CAGGAAACAGCTATGACACAATAAAACCATCCCAAATAC |
| C | ER1-B-U-M13b | CAGGAAACAGCTATGACAGGAGGGGGAATTAAATAGA |
| D | ER1-B-L-M13a | GTAAAACGACGGCCAGTACAATAAAACCATCCCAAATAC |
| E | ER1-B-U | AGGAGGGGGAATTAAATAGA |
| F | ER1-B-L | ACAATAAAACCATCCCAAATAC |
| G | M13a | GTAAAACGACGGCCAGT |
| H | M13b | CAGGAAACAGCTATGAC |

The PCR products produced with the primer combinations ER1-B-L-M13b/ER1-B-L-M13a, ER1-B-U-M13a/ER1-B-L-M13a, ER1-B-L-M13b/ER1-B-U-M13b and ER1-B-U/ER1-B-L (see FIG. 3) were reamplified with Qiagen Hotstart Polymerase according to the manufacturer's instructions (Qiagen, Hilden) in a reaction volume of 25 µl with the primers M13a or M13b or a mixture of these primers. In this way, the PCR products from the PCR reaction (see FIG. 3) were diluted 1:1000 and amplified in the following PCR reactions.

Reaction Batch (General):

With the Use of One Primer

| | |
|---|---|
| DNA (1:1000 diluted PCR fragment) | 1 µl |
| Reaction buffer 10x (Qiagen, Hilden) | 2.5 µl |
| dNTP mix (25 mM each) | 0.2 µl |
| Primer 12.5 pmol/µl | 2 µl |
| Polymerase (Qiagen, Hilden) (0.5 U) | 0.2 µl |
| Water | 19.1 µl |

With the Use of a Pair of Primers

| | |
|---|---|
| DNA (1:1000 diluted PCR fragment) | 1 µl |
| Reaction buffer 10x (Qiagen, Hilden) | 2.5 µl |
| dNTP mix (25 mM each) | 0.2 µl |
| Primer 1 12.5 pmol/µl | 2 µl |
| Primer 2 12.5 pmol/µl | 1 µl |
| Polymerase (Qiagen, Hilden) (0.5 U) | 0.2 µl |
| Water | 19.1 µl |

The PCR reaction was conducted in the Master Cycler Gradient (Eppendorf, Hamburg) with the following program: 15 min 96° C.; 60 s 96° C. (×40); 45 s 55° C. (×40); 75 s 72° C. (×40); 10 min 72° C.

The reamplification supplied the expected results (see FIG. 4). With the mixture of the generic primers M13a/M13b, the PCR products of the primer combinations ER1-B-L-M13b/ER1-B-L-M13a, ER1-B-U-M13a/ER1-B-LM13a and ER1-B-L-M13b/ER1-B-U-M13b could be reamplified. The reamplifications of the PCR produts of the primer combinations ER1-B-U-M13a/ER1-B-L-M13a could also be conducted with the primer M13a, and those of the primer combinations ER1-B-LM13b/ER1-B-U-M13b with the primer M13b. The PCR product which was obtained with the non-modular primer combination ER1-B-U/ER1-B-L, could not be reamplified, as expected, with generic primers or a combination of the primers M13a/M13b (see FIG. 4: Analysis of the ESR1 PCR products in a 1.5% agarose gel (Manniatis et al.).

FIG. 3: Four microliters each from the PCR reactions of primer combination ER1-B-L-M13b/ER1-B-L-M-13a (lanes 1, 5), ER1-B-U-M13a/ER1-B-L-M13a (lanes 2, 6), ER1-B-L-M13b/ER1-B-U-M13b (lanes 3, 7) and ER1-B-U/ER1-B-L (lanes 4, 8) on bisulfite-treated DNA (lanes 1-4) and untreated genomic DNA (lanes 5-8) were analyzed. Lane M is a DNA fragment size standard.

AGGAGGGGGAATTAAATAGAAAGAGAGATAAATAGAGATATATCGGAGTT

TGGTACGGGGTATATAAGGTAGTATATTAGAGAAAGTCGGTTTTTGGATT

CGTTTTTCGCGTTTATTTTAAGTTTAGTTTTTTTGGGTTATTTTTAGTA

GATTTTCGTGCGTTTTCGTTTTTTGGTCGTGAAATTTAGTTTTTATTTAG

TAGCGACGATAAGTAAAGTAAAGTTTAGGGAAGTTGTTTTTTGGGATGTT

TAAATCGAGTTGTGTTTGGAGTGATGTTTAAGTTAATGTTAGGGTAAGGT

AATAGTTTTTGGTCGTTTTTTAGTATTTTTGTAATGTATATGAGTTCGGG

-continued

AGATTAGTATTTAAAGTTGGAGGTTCGGGAGTTTAGGAGTTGGCGGAGGG

CGTTCGTTTTGGGATTGTAT1TGTTTTCGTCGGGTCGTTCGGTTTTATCG

GATTCGTAGGTTTTCGGGGTAGGGTCGGGGTTAGAGTTCGCGTGTCGGCG

GGATATGCGTTGCGTCGTTTTTAATTTCGGGTTGTGTTTTTTTTTAGGT

GGTTCGTCGGTTTTTGAGTTTTTTGTTTTG)CGGGGATACGGTTTGTATT

TTGTTCGCGGTTACGGATTATGATTATGATTTTTTATATTAAAGTATTTG

GGATGGTTTTATTGT

FIG. 4: Analysis of the reamplification of the ESR1 PCR products (see FIG. 4) in a 1.5% agarose gel (Manniatis et al.). The reamplification of the PCR products was investigated for the primer combinations ER1-B-U/ER1-B-L (lanes 2, 7, 12), ER1-B-L-M13b/ER1-B-L-M13a (lanes 3, 8, 13), ER1-B-U-M13a/ER1-B-L-M13a (lanes 4, 8, 14) and ER1-B-L-M13b/ER1-B-U-M13b (lanes 5, 10, 15) with generic primers and primer combinations. Each time, 4 µl from the PCR reactions with the generic primer combination M13a/M13b (lanes 1-5), the generic primer M13a (lanes 6-10) and the generic primer M13b (lanes 11-15) are represented. Lane M is a DNA fragment size standard.

APPENDIX

Figure 1:
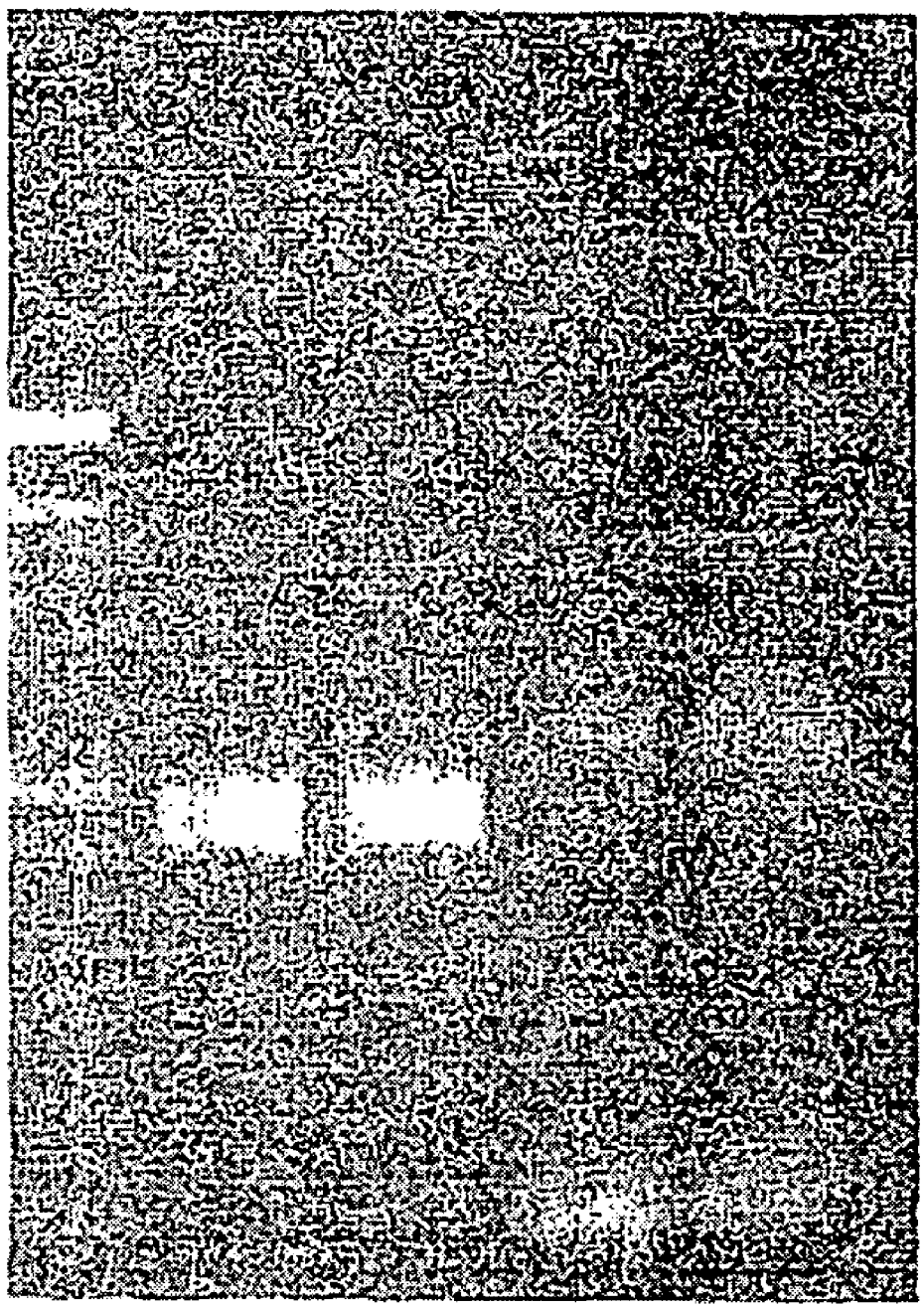
FIG. 1: Gene-specific amplification of OAT and MDR1.
M, Size marker,
A, Amplification of OAT (primers: OAT-f1mp and OAT-rmp),
B, Amplification of OAT (primers: OAT-f2mp and OAT-rmp),
C, Amplification of MDR1 (primers: MDR-f1mp and MDR-rmp), and
D, Amplification of MDR1 (primers: MDR-f2mp and MDR-rmp).
Figure 2:
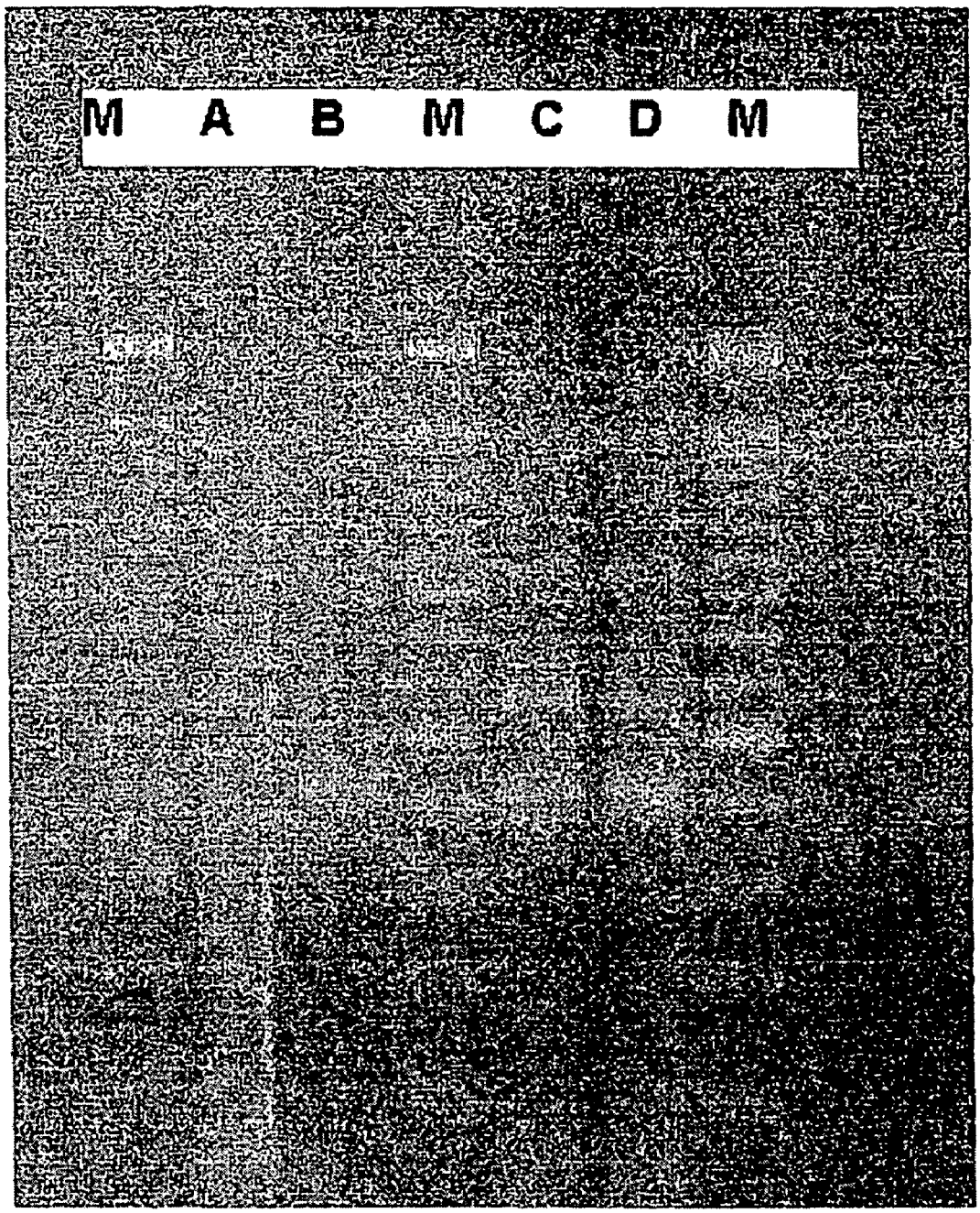
FIG. 2: Reamplification of OAT/Mdr1-fragments from Example 2 with generic primers
M, Size marker,
A, MDR1 with primers gen1-fp5 and gen-rp;
B, OAT with primers gen1-fp5 and gen-rp;
C, MDR1 and OAT with primers gen1-fp5 and gen-rp;
D, MDR1 and OAT with primers gen2-fp5 and gen-rp.
Figure 3:
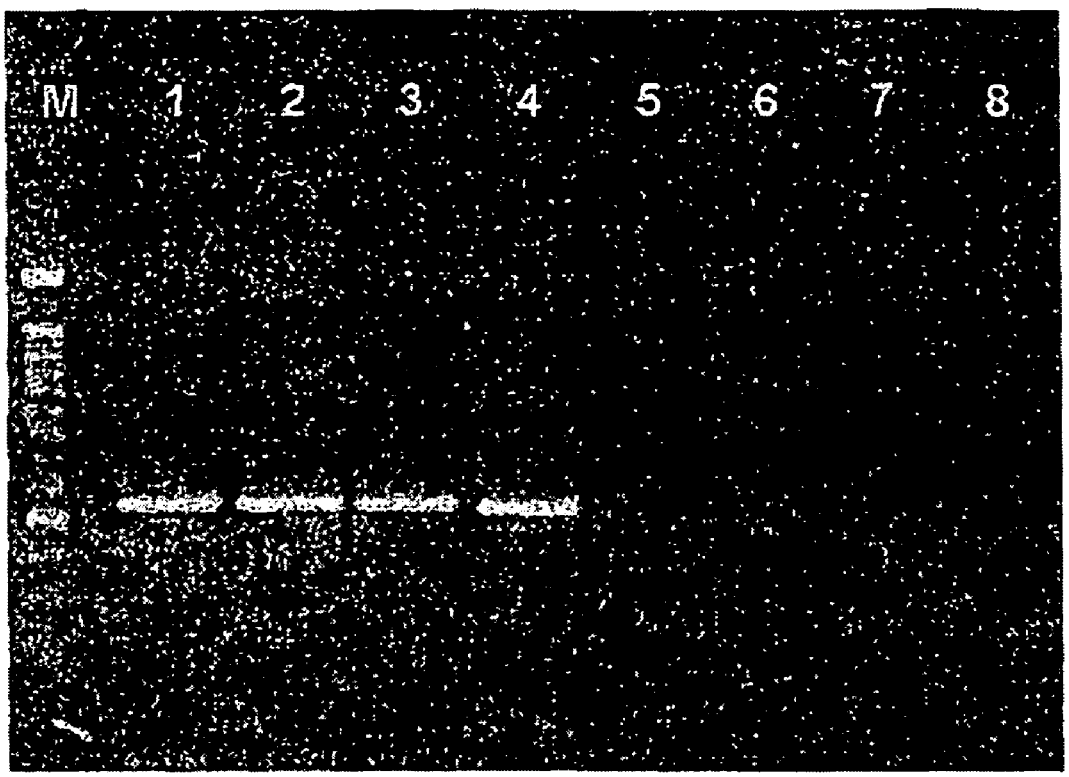
FIG. 3: Four microliters each from the PCR reactions of primer combination ER1-B-L-M13b/ER1-B-L-M-13a (lanes 1, 5), ER1-B-U-M13a/ER1-B-L-M13a (lanes 2, 6), ER1-B-L-M13b/ER1-B-U-M13b (lanes 3, 7) and ER1-B-U/ER1-B-L (lanes 4, 8) on bisulfite-treated DNA (lanes 1-4) and untreated genomic DNA (lanes 5-8) were analyzed. Lane M is a DNA fragment size standard.
Figure 4:
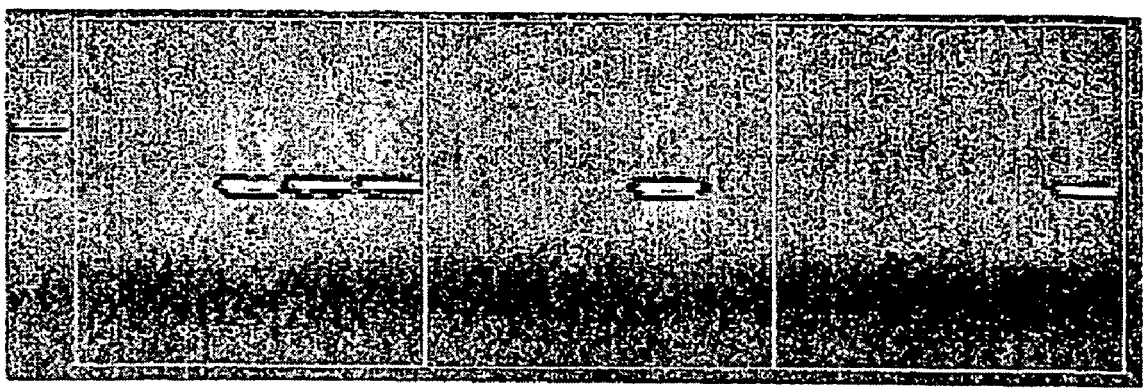
FIG. 4: Analysis of the reamplification of the ESR1 PCR products (see FIG. 4) in a 1.5% agarose gel (Manniatis et al.).

Sequences of OAT and MDR1 After Treatment with Bisulfite

Mdr1 (SEQ ID NO: 24):
    0    GTTAAGAATA AAATATATTA AGATAAGGAA
         AATTTGTAGT TAAGAATAGA AAAAAATTAT

-continued

```
  60  GGTTTTGAAG TATGAGTTAT TTAAAGAAAG
      TGGAAATATT TTTAGATTAT GTAGTAAAAA
 120  ATAAAGTGAT TTTTTTTTTT TAAATTTATG
      TAATAAATTG ATAGGTAATA TGTGAAAGTT
 190  ATAGAATGTA GATTAGAGGA TATAATAAAT
      TTATTTTTTT TATGTTTATA AGAAGTAAGA
 240  AAAGTTTTGA TGTGAGTTAG TATTGTTTTA
      TAATTTTGAA TTGTGTAGAT TGTACGTATT
 300  TTTTTTTAGT TTGAAGTAAA TAGTGGATAG
      GAAAAAATAT TAAATGTTGG TAGTAAATAT
 360  GGAAGGAAAT TATAATTAAT GTAATATGTT
      AAAATATGTT ATGTTTATTT TATTAATTTG
 420  AATTAAAATG TAAGAATTTA AAATGTTTTG
      GAAAAATACG GGTATTGATT TGACGTTGA
 480  AGTTTTAAAA TATTATATAT TTTGAAATAG
      TATTTGTATT TTGAAATATT TGTTTTTATA
 540  TATTTTTTAA AATTTTTTTT TTTTTTATT
      TTATTTATTA TTAAATAAAG GATGAATAGA
 600  TGTAATTTAG AAATTGTTAA GTATGTTGAA
      GAAAGATTAT TGTAGAAAAA TTTTTTTAG
 660  TTTTTTTAAA GGTGTTAGGA AGTAGAAAGG
      TGATATAGAA TTGGAGAGGT CGGAGTTTTT
 720  GTATTAATTG TATTAAATGC GAATTTCGAG
      AAAATTTTTT TTAATTACGT TTTGTAGTTA
 780  TATGGATATG AAGATTTATG TGAATTTTGA
      AAGACGTGTT TATATAAGTT GAAATGTTTT
 840  TAATGATTTA GTTGATGCGC GTTTTTTAT
      TTGTTTTTTT TAGAGAGGTG TAACGGAAGT
 900  TAGAATATTT TTTTTGGAAA TTTAATTTGT
      TTCGTAGTTT TTCGAGGAAT TAGTATTTAG
 960  TTAATTCGGG TCGGGAGTAG TTATTTGTGG
      TGAGGTTGAT TGGTTGGGTA GGAATAGCGT
1020  CGGGGCGTGG GTTGAGTATA GTCGTTTCGT
      TTTTTTTGTT ATAGGAAGTT TGAGTTTATT
1080  CGAGTAGCGG TTTTTTTAAG TTTAAAGAAG
      TAGAGGTCGT TGTTCGTTTT TTTTAGGTTT
1140  TTTTATTAAA GTCGGAGTAT TTTTTTTTAA
      AATTTTACGT TTTGGTGGTC GTTTTAAGGA
1200  GCGCGAGGTA GGGGTACGTA AAGTTGGGAG
      TTATTATGGG ATAGTTTTTA AGTGTTAGGT
1260  TTTTAGATTT TTTGAATTTG GTTTTTACGG
      GAGAAGGGTT TTTTGAGGCG TGGATAGTGT
1320  GAAGTTTTTT GGTAAGTTTA TGGGGATTAA
      GTGGGGTTAG ATTTAGATTT AGGAGTTTTT
1380  GGAGTAGCGT TTAAATCGTA GTGGTATTGG
      ATTATGTTGT TCGGAGCGCG TATAGTTCGC
1440  GCGGTGCGGG GATTTGTTTT TTGAGTTCGC
      GGGCGGTGGG TGGGAGGAAG TATCGTTCGC
1500  GGCGATTGGA ATCGGGAGGG AGAATCGTAT
      TGGCGGCGGG TAAAGTTTAG AACGCGTTGT
1560  TAGATTTTTA ATTTTGTTTT CGTGGAGATG
      TTGGAGATTT CGCGTATAGG AAAGTTTTTG
1620  TAGTGTTTAT CGCGGTTAGA GTAGTTGGGG
      TATTAACGGC GGGCGTTTTT TTTTATTGTT
1680  TTTTGGTTTC GACGGGGGAT TAGAGGTTAG
      TTTTATTTTT AGCGCGTTTG AGGTTTATGT
1740  ATTTGGTTAA TGAGTTGCGG TTTTTTTTTA
      GGTCGGGATG GATTTTGAAG GGGATCGTAA
1800  TGGAGGAGTA AAGAAGAAGA ATTTTTTTAA
      ATTGAATAAT AAAAGGTAAT TAGTTTGTTT
1860  TATTTTTATA GTTTATATAG TTGCGAGATT
      TGAGTAATTT ATTTTTAGTT TTTAGTTTTG
1920  AAATAAATGA TATGTTGTTG TTTTTAATTA
      TTTTTAAGAA ACGTAAGTTA GTTTTTGGAA
1980  TTAATATTTT TGTTTAGAGT AGAAGTTTGT
      TGGTTGAGTG GAGTATAGTA TATGTATTTT
2040  TTTTGTTTTT TTTGTTTTTT TTTTTAATGA
      TATATAATAT TTTATATATT TATGAAATGG
2100  GGTATATGGA AGCGTTTTTT ATATGTTCGG
      AATGTGTAAT GATTAAGTTC GGGTATTTGA
2160  AGGATATATT ATTTTAGGTA TATTTTATTT
      TTATGTGTTG ATAATATTTT AAGTTTTTTA
2220  GTTATTTTGA AATATATAAT ATATTGTTAA
      TTGTAGTTAT TTTCGTTTGT TATCGAATAT
2280  TGGAATTTAT TTGTTTTATT TAATCGTTTT
      TAGTTATTTA TTAATTTTTT TTTATTTTAT
2340  TTTTTTATTT TTTTCGGTTT TTTTTTTTA
      GTTTTGGTGT GTTTTTTTTT TAGTTTTTTT
2400  GTTTTAGATA GGCGGATGTT TATATGTGTT
      TTTGTTTTAT GAATTTTTGT TTTTTAAGTG
2460  GTGTTGGTCG TTTATACGTG AGTTATATGT
      TGTTGGTGAT TTGTTTTGTG GTTTAGGTTT
2520  TTGTTTTCGG TAAATGGTTA TGTAAATATC
      GCGTTTGTGG TTTGGTTGAT GAGATAGAAG
2580  GTTAAAAGTA TATTTAGGTT GTTAATTGGT
      AATAAATATT TGTATATAAT ATTGGTAATG
2640  TAATTATATA GGGAAAATAA TTATTTAAAG
      TAAATTTTGA TTATGGTGTT TTGTTTTTAT
2700  AGAATATTTA AAATTTTATT AAATAGATTT
      ATTGTTAGTA GTAAATTGTA AAATAGATTA
2760  GTAAGTTTAA TAATATTAGA AATTGTAATG
      TAAATTATAA GATAAATTAG TTAAATATAT
2820  TAATATTATA AGAAATTAAG TTTTTTAGTG
      TAAGAGAAAA AATATAAATG TGGAAATTAA
2880  ATATATTTTT AAAAATAATG TTAAGTTTGA
      ATTAGAAATT TTAATATGAA TT

OAT (SEQ ID NO 25):
   1  GGTAGCGACG ATTTTGGAG GTGGATTTAG
      AGGTATAATT AAGTCGCGCG GCGTATTAGG
  61  GTTTAAGGGT ATGGGGTTTT CGTAGTTGTG
      GTTGGGGTAG AGTTGGGGTT GTTTTTTTTT
 121  TTAGGAGTAT AGGCGGCGGT TTAGTTTTAC
      GTTTTTCGTT TTTAGTTATA TTCGGTTCGC
 181  GTAGTGGGGG GTTTAATAGA TTTTTTTTTT
      TCGGGTTTTA GTTTTTTCGT TAGTAAGGGC
```

-continued

```
241  GGATAAGGAT TTTTTTCGTT TCGTTAGAGG
     AGGCGATCGA GGGGTTTGAG TTTAGGTATA

301  GGTCGGCGGG TTTAGGAGGC GCGAGGCGGA
     TCGAATTCGC GGGAGGAGTA AAGATTTTTG

361  ATGCGCGGTC GGAGGGCGGG GCGGAGGACG
     GGATTTACGC GATTGGTATT TTGTTTTTCG
```

-continued

```
421  TTTTAGTTAA TGAGCGGCGA GGGTGTTTTG
     GGGGCGGGGT AGAATTAGTT TTTAAGTTGT

481  AGTGACGTTT CGGCGTTATT GTTGCGTTTT
     ATAGACGTCG CGTGTATTCG GTTGTTTTTA

541  GGCGTTGTTA GGTATCGTTT GGGCGTCGTT
     GTTTTGGGGT TTTGGTTCGG GTTTGGTCGG

601  AAACGTCACT ACAACTAAAA AACTAA
```

---

The invention claimed is:

1. A method for the amplification of nucleic acids, said method consisting of the following steps:
   a) a nucleic acid is chemically converted with a reagent, whereby 5-methylcytosine remains unchanged and cytosine is converted to uracil or another base similar to uracil in its base-pairing behavior,
   b) the segments to be amplified of the converted nucleic acid are hybridized with at least two first primer oligonucleotides, which have two domains: the sequence-specific domain found on the 3'-end hybridizes to the segment to be analyzed, while the generic domain found on the 5'-end does not hybridize,
   c) a first amplification reaction is conducted by means of a polymerase,
   d) two second primer oligonucleotides which hybridize to the generic domains of the first primer oligonucleotides and hybridize to the amplificate generated in step (c), wherein one of said two second primer oligonucleotides is labeled, and
   e) the sequence of the amplificate is investigated.

2. The method according to claim 1, further characterized in that after step c) of claim 1, a second amplification with a polymerase chain reaction is additionally conducted.

3. The method according to claim 1, further characterized in that the generic domain of the primers contains the nucleobases A, C, G and T, while the sequence-specific domain contains either only the bases A, T and C or only the bases A, T and G.

4. The method according to claim 1, further characterized in that the reagent involves a bisulfite.

5. The method according to claim 4, further characterized in that the chemical treatment is conducted after embedding the nucleic acid in agarose.

6. The method according to claim 4, further characterized in that in the chemical treatment, a reagent that denatures a duplex nucleic acid and/or a radical trap are added.

7. The method according to claim 1, further characterized in that the labeling of oligonucleotide primers involves fluorescent dyes with different emission spectra or fluorescent dye combinations in the case of primers labeled by energy-transfer fluorescent dye.

8. The method according to claim 1, further characterized in that the labels are radionuclides.

9. The method according to claim 1, further characterized in that the labels are removable mass labels which are detected in a mass spectrometer.

10. The method according to claim 1, further characterized in that molecules that only produce a signal in a further chemical reaction are used for the label.

11. The method according to claim 1, further characterized in that molecules which are immobilized at defined positions on a solid phase are used for the label.

12. The method according to claim 1, further characterized in that the PCR fragments are arranged on a solid phase in the form of a rectangular or hexagonal grid.

13. The method according to claim 1, further characterized in that labels that are introduced on the amplificates at each position of the solid phase at which an oligonucleotide sequence is found can be identified.

14. The method according to claim 1, further characterized in that a heat-stable DNA polymerase is used for the amplification.

15. The method according to claim 1, wherein the nucleic acids were obtained from a genomic DNA sample, whereby sources for DNA include, e.g., cell lines, blood, sputum, stool, urine, cerebrospinal fluid, tissue embedded in paraffin, for example, tissue from eyes, intestine, kidney, brain, heart, prostate, lung, breast or liver, histological slides and all possible combinations thereof.

* * * * *

SEQUENCE LISTING

<160> NUMBER OF SEQ ID NOS: 27

<210> SEQ ID NO 1
<211> LENGTH: 29
<212> TYPE: DNA
<213> ORGANISM: Artificial Sequence
<220> FEATURE:
<223> OTHER INFORMATION: Primer

<400> SEQUENCE: 1
tttggaggtg gatttagagg tataattaa                                    29

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aaacrtcact acaacttaaa aactaa                                       26

<210> SEQ ID NO 3
<211> LENGTH: 28
<212> TYPE: DNA
<213> ORGANISM: Artificial Sequence
<220> FEATURE:
<223> OTHER INFORMATION: Primer

<400> SEQUENCE: 3
taagtatgtt gaagaaagat tattgtag                                     28

<210> SEQ ID NO 4
<211> LENGTH: 28
<212> TYPE: DNA
<213> ORGANISM: Artificial Sequence
<220> FEATURE:
<223> OTHER INFORMATION: Primer

<400> SEQUENCE: 4
taaaaactat cccataataa ctcccaac                                     28

<210> SEQ ID NO 5
<211> LENGTH: 17
<212> TYPE: DNA
<213> ORGANISM: Artificial Sequence
<220> FEATURE:
<223> OTHER INFORMATION: Primer

<400> SEQUENCE: 5
gtaaaacgac ggccagt                                                 17

-continued

```
<210> SEQ ID NO 6
<211> LENGTH: 17
<212> TYPE: DNA
<213> ORGANISM: Artificial Sequence
<220> FEATURE:
<223> OTHER INFORMATION: Primer

<400> SEQUENCE: 6
gtaaaaccag ggccagt                                                    17

<210> SEQ ID NO 7
<211> LENGTH: 17
<212> TYPE: DNA
<213> ORGANISM: Artificial Sequence
<220> FEATURE:
<223> OTHER INFORMATION: Primer

<400> SEQUENCE: 7
caggaaacag ctatgac                                                    17

<210> SEQ ID NO 8
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_binding
<222> LOCATION: (1)..(1)
<223> OTHER INFORMATION: labelled with Cy5

<400> SEQUENCE: 8
gtaaaacgac ggccagt                                                    17

<210> SEQ ID NO 9
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_binding
<222> LOCATION: (1)..(1)
<223> OTHER INFORMATION: labelled with cy5

<400> SEQUENCE: 9
gtaaaaccag ggccagt                                                    17

<210> SEQ ID NO 10
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_binding
<222> LOCATION: (1)..(1)
<223> OTHER INFORMATION: labelled with cy5

<400> SEQUENCE: 10
caggaaacag ctatgac                                                    17

<210> SEQ ID NO 11
<211> LENGTH: 17
<212> TYPE: DNA
<213> ORGANISM: Artificial Sequence
<220> FEATURE:
```

<223> OTHER INFORMATION: Primer

<400> SEQUENCE: 11
caggaaacag ctatgac                                                        17

<210> SEQ ID NO 12
<211> LENGTH: 45
<212> TYPE: DNA
<213> ORGANISM: Artificial Sequence
<220> FEATURE:
<223> OTHER INFORMATION: Primer

<400> SEQUENCE: 12
gtaaaaccag ggccagtttg gaggtggatt tagaggtata attaa           45

<210> SEQ ID NO 13
<211> LENGTH: 43
<212> TYPE: DNA
<213> ORGANISM: Artificial Sequence
<220> FEATURE:
<223> OTHER INFORMATION: Primer

<400> SEQUENCE: 13
caggaaacag ctatgacaaa crtcactaca acttaaaaac taa                 43

<210> SEQ ID NO 14
<211> LENGTH: 45
<212> TYPE: DNA
<213> ORGANISM: Artificial Sequence
<220> FEATURE:
<223> OTHER INFORMATION: Primer

<400> SEQUENCE: 14
gtaaaacgac ggccagttaa gtatgttgaa gaaagattat tgtag             45

<210> SEQ ID NO 15
<211> LENGTH: 45
<212> TYPE: DNA
<213> ORGANISM: Artificial Sequence
<220> FEATURE:
<223> OTHER INFORMATION: Primer

<400> SEQUENCE: 15
gtaaaaccag ggccagttaa gtatgttgaa gaaagattat tgtag             45

<210> SEQ ID NO 16
<211> LENGTH: 45
<212> TYPE: DNA
<213> ORGANISM: Artificial Sequence
<220> FEATURE:
<223> OTHER INFORMATION: Primer

<400> SEQUENCE: 16
caggaaacag ctatgactaa aaactatccc ataataactc ccaac             45

<210> SEQ ID NO 17
<211> LENGTH: 37
<212> TYPE: DNA
<213> ORGANISM: Artificial Sequence
<220> FEATURE:
<223> OTHER INFORMATION: Primer

<400> SEQUENCE: 17
gtaaaacgac ggccagtagg aggggaatt aaataga                         37

<210> SEQ ID NO 18
<211> LENGTH: 39
<212> TYPE: DNA
<213> ORGANISM: Artificial Sequence
<220> FEATURE:
<223> OTHER INFORMATION: Primer

<400> SEQUENCE: 18
caggaaacag ctatgacaca ataaaaccat cccaaatac        39

<210> SEQ ID NO 19
<211> LENGTH: 37
<212> TYPE: DNA
<213> ORGANISM: Artificial Sequence
<220> FEATURE:
<223> OTHER INFORMATION: Primer

<400> SEQUENCE: 19
caggaaacag ctatgacagg aggggggaatt aaataga        37

<210> SEQ ID NO 20
<211> LENGTH: 39
<212> TYPE: DNA
<213> ORGANISM: Artificial Sequence
<220> FEATURE:
<223> OTHER INFORMATION: Primer

<400> SEQUENCE: 20
gtaaaacgac ggccagtaca ataaaaccat cccaaatac        39

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
aggaggggga attaaataga        20

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
acaataaaac catcccaaat ac        22

<210> SEQ ID NO 23
<211> LENGTH: 664
<212> TYPE: DNA
<213> ORGANISM: Artificial  Sequence
<220> FEATURE:
<223> OTHER INFORMATION: PCR product

<400> SEQUENCE: 23
aggaggggga attaaataga aagagagata aatagagata tatcggagtt tggtacgggg        60
tatataaggt agtatattag agaaagtcgg tttttggatt cgttttcgc gttattttta        120 agtttagttt tttttgggtt attttagta gattttcgtg cgttttcgtt ttttggtcgt        180
gaaatttagt tttatttag tagcgacgat aagtaaagta aagtttaggg aagttgtttt        240
ttgggatgtt taaatcgagt tgtgtttgga gtgatgttta agttaatgtt agggtaaggt        300

-continued

| | |
|---|---|
| aatagttttt ggtcgttttt tagtattttt gtaatgtata tgagttcggg agattagtat | 360 |
| ttaaagttgg aggttcggga gtttaggagt tggcggaggg cgttcgtttt gggattgtat | 420 |
| ttgttttcgt cgggtcgttc ggttttatcg gattcgtagg ttttcggggt agggtcgggg | 480 |
| ttagagttcg cgtgtcggcg ggatatgcgt tgcgtcgttt ttaatttcgg gttgtgtttt | 540 |
| tttttaggt ggttcgtcgg tttttgagtt ttttgttttg cggggatacg gtttgtattt | 600 |
| tgttcgcggt tacggattat gattatgatt ttttatatta aagtatttgg gatggtttta | 660 |
| ttgt | 664 |

<210> SEQ ID NO 24
<211> LENGTH: 2932
<212> TYPE: DNA
<213> ORGANISM: Artificial Sequence
<220> FEATURE:
<223> OTHER INFORMATION: bisulphite treated sequence

<400> SEQUENCE: 24

| | |
|---|---|
| gttaagaata aaatatatta agataaggaa aatttgtagt taagaataga aaaaaattat | 60 |
| ggttttgaag tatgagttat ttaaagaaag tggaaatatt tttagattat gtagtaaaaa | 120 |
| ataaagtgat tttttttttt taaatttatg taataaattg ataggtaata tgtgaaagtt | 180 |
| atagaatgta gattagagga tataataaat ttatttttt tatgtttata agaagtaaga | 240 |
| aaagttttga tgtgagttag tattgtttta taattttgaa ttgtgtagat tgtacgtatt | 300 |
| tttttttagt ttgaagtaaa tagtggatag gaaaaaatat taaatgttgg tagtaaaatat | 360 |
| ggaaggaaat tataattaat gtaatatgtt aaaatatgtt atgtttattt tattaatttg | 420 |
| aattaaaatg taagaattta aaatgttttg gaaaaatacg ggtattgatt tgacgtttga | 480 |
| agttttaaaa tattatatat tttgaaatag tatttgtatt ttgaaatatt tgtttttata | 540 |
| tattttttaa aattttttt ttttttatt ttatttatta ttaaataaag gatgaataga | 600 |
| tgtaatttag aaattgttaa gtatgttgaa gaaagattat tgtagaaaaa ttttttttag | 660 |
| tttttttaaa ggtgttagga agtagaaagg tgatatagaa ttggagaggt cggagttttt | 720 |
| gtattaattg tattaaatgc gaatttcgag aaaattttt ttaattacgt tttgtagtta | 780 |
| tatggatatg aagattatg tgaattttga agacgtgtt tatataagtt gaaatgtttt | 840 |
| taatgattta gttgatgcgc gttttttat ttgttttttt tagagaggtg taacggaagt | 900 |
| tagaatattt tttttggaaa tttaatttgt ttcgtagttt ttcgaggaat tagtatttag | 960 |
| ttaattcggg tcgggagtag ttatttgtgg tgaggttgat tggttgggta ggaatagcgt | 1020 |
| cggggcgtgg gttgagtata gtcgtttcgt ttttttgtt ataggaagtt tgagtttatt | 1080 |
| cgagtagcgg ttttttaag tttaaagaag tagaggtcgt tgttcgtttt tttaggttt | 1140 |
| ttttattaaa gtcggagtat ttttttttaa aattttacgt tttggtggtc gttttaagga | 1200 |
| gcgcgaggta ggggtacgta aagttgggag ttattatggg atagttttta agtgttaggt | 1260 |
| ttttagattt tttgaatttg gtttttacgg gagaagggtt tttgaggcg tggatagtgt | 1320 |
| gaagttttt ggtaagttta tgggattaa gtggggttag atttagattt aggagttttt | 1380 |
| ggagtagcgt ttaaatcgta gtggtattgg attatgttgt tcggagcgcg tatagttcgc | 1440 |
| gcggtgcggg gatttgtttt ttgagttcgc gggcggtggg tggaggaag tatcgttcgc | 1500 |
| ggcgattgga atcgggaggg agaatcgtat tggcggcggg taaagtttag aacgcgttgt | 1560 |
| tagattttta attttgtttt cgtggagatg ttggagattt cgcgtatagg aaagtttttg | 1620 |
| tagtgtttat cgcggttaga gtagttgggg tattaacggc gggcgttttt tttattgtt | 1680 |

```
ttttggtttc gacggggat  tagaggttag  ttttattttt  agcgcgtttg  aggtttatgt    1740
atttggttaa  tgagttgcgg  tttttttta  ggtcgggatg  gattttgaag  gggatcgtaa    1800
tggaggagta  aagaagaaga  attttttaa  attgaataat  aaaaggtaat  tagtttgttt    1860
tatttttata  gtttatatag  ttgcgagatt  tgagtaattt  attttagtt  tttagttttg    1920 aaataaatga  tatgttgttg  tttttaatta  tttttaagaa  acgtaagtta  gttttggaa     1980 ttaatatttt  tgtttagagt  agaagtttgt  tggttgagtg  gagtatagta  tatgtattt     2040 ttttgttttt  tttgtttttt  tttttaatga  tatataatat  tttatatatt  tatgaaatgg    2100
ggtatatgga  agcgtttttt  atatgttcgg  aatgtgtaat  gattaagttc  gggtatttga    2160
aggatatatt  attttaggta  tattttattt  ttatgtgttg  ataatatttt  aagttttta    2220 gttattttga  aatatataat  atattgttaa  ttgtagttat  tttcgtttgt  tatcgaatat    2280
tggaatttat  ttgttttatt  taatcgtttt  tagttattta  ttaatttttt  tttattttat    2340
tttttatttt  ttttcggttt  tttttttta  gttttggtgt  gtttttttt  tagttttttt    2400 gttttagata  ggcggatgtt  tatatgtgtt  tttgttttat  gaatttttgt  tttttaagtg    2460
gtgttggtcg  tttatacgtg  agttatatgt  tgttggtgat  ttgttttgtg  gtttaggttt    2520 ttgtttttcgg  taaatggtta  tgtaaatatc  gcgtttgtgg  tttggttgat  gagatagaag    2580
gttaaaagta  tatttaggtt  gttaattggt  aataaatatt  tgtatataat  attggtaatg    2640
taattatata  gggaaaataa  ttatttaaag  taaattttga  ttatggtgtt  ttgttttat    2700 agaatatta  aaatttatt   aaatagattt  attgttagta  gtaaattgta  aaatagatta    2760
gtaagtttaa  taatattaga  aattgtaatg  taaattataa  gataaattag  ttaaatatat    2820
taatattata  agaaattaag  ttttttagtg  taagagaaaa  aatataaatg  tggaaattaa    2880
atatattttt  aaaaataatg  ttaagtttga  attagaaatt  ttaatatgaa  tt             2932
```

<210> SEQ ID NO 25
<211> LENGTH: 626
<212> TYPE: DNA
<213> ORGANISM: Artificial Sequence
<220> FEATURE:
<223> OTHER INFORMATION: bisulphite treated sequence

<400> SEQUENCE: 25

```
ggtagcgacg  attttttggag  gtggatttag  aggtataatt  aagtcgcgcg  gcgtattagg    60
gtttaagggt  atgggttttt  cgtagttgtg  gttggggtag  agttgggtt   gttttttttt   120 ttaggagtat  aggcggcggt  ttagttttac  gttttcgtt   tttagttata  ttcggttcgc   180
gtagtggggg  gttaatagaa  tttttttttt  tcgggtttta  gttttttcgt  tagtaagggc   240
ggataaggat  ttttttcgtt  tcgttagagg  aggcgatcga  ggggtttgag  tttaggtata   300
ggtcggcggg  tttaggaggc  gcgaggcgga  tcgaattcgc  gggaggagta  aagattttg    360 atgcgcggtc  ggagggcggg  gcggaggacg  ggatttacgc  gattggtatt  tgttttcg    420 ttttagttaa  tgagcggcga  gggtgttttg  ggggcgggt   agaattagtt  tttaagttgt   480
agtgacgttt  cggcgttatt  gttgcgtttt  atagacgtcg  cgtgtattcg  gttgttttta   540
ggcgttgtta  ggtatcgttt  gggcgtcgtt  gttttggggt  tttggttcgg  gtttggtcgg   600
aaacrtcact  acaacttaaa  aactaa                                          626
```

<210> SEQ ID NO 26
<211> LENGTH: 45
<212> TYPE: DNA

```
-continued

<213> ORGANISM: Artificial Sequence
<220> FEATURE:
<223> OTHER INFORMATION: Primer

<400> SEQUENCE: 26
gtaaaacgac ggccagtttg gaggtggatt tagaggtata attaa                45

<210> SEQ ID NO 27
<211> LENGTH: 17
<212> TYPE: DNA
<213> ORGANISM: Artificial Sequence
<220> FEATURE:
<223> OTHER INFORMATION: Primer

<400> SEQUENCE: 27
gtaaaacgag ggccagt                                               17
```